United States Patent [19]

Prince et al.

[11] Patent Number: 4,657,529
[45] Date of Patent: Apr. 14, 1987

[54] BLOOD EXTRACTION AND REINFUSION FLOW CONTROL SYSTEM AND METHOD

[75] Inventors: Paul R. Prince, Fountain Valley; Ronald L. Clark, Westminster, both of Calif.

[73] Assignee: Hemascience Laboratories, Inc., Santa Ana, Calif.

[21] Appl. No.: 801,131

[22] Filed: Nov. 22, 1985

Related U.S. Application Data

[63] Continuation-in-part of Ser. No. 626,034, Jun. 29, 1984, abandoned.

[51] Int. Cl.$^4$ ............................................. A61M 1/03
[52] U.S. Cl. .......................................... 604/6; 604/66; 128/DIG. 13
[58] Field of Search ....................................... 604/4–7, 604/55, 65–67, 245; 128/DIG. 13

[56] References Cited

U.S. PATENT DOCUMENTS

| | | | |
|---|---|---|---|
| 3,949,734 | 4/1976 | Edwards et al. | 604/4 X |
| 4,086,924 | 5/1978 | Latham, Jr. | 604/6 |
| 4,285,464 | 8/1981 | Latham, Jr. | 604/6 X |
| 4,401,431 | 8/1983 | Arp | 604/4 |
| 4,447,191 | 5/1984 | Bilstad et al. | 604/6 X |
| 4,468,219 | 8/1984 | George et al. | 604/66 |
| 4,481,827 | 11/1984 | Bilstad et al. | 604/6 X |

*Primary Examiner*—Edward M. Coven
*Attorney, Agent, or Firm*—Bogucki, Scherlacher, Mok & Roth

[57] ABSTRACT

A blood extraction and reinfusion flow control system includes a blood pump coupled to pump intravenous fluid to or from a subject, a pressure sensor coupled to sense extra veinous pressure at the subject, and a microprocessor based flow control subsystem. The flow control subsystem optimizes the flow rate by sensing pressure at at least two different fluid flow test points and extrapolating and translating the test point data to generate a flow control curve. The blood pump is then operated at a maximum speed that is limited by a desired maximum flow command and the flow control curve to maximize flow without vein collapse or damage during both blood extraction and reinfusion.

48 Claims, 7 Drawing Figures

BLOOD EXTRACTION AND REINFUSION FLOW CONTROL SYSTEM AND METHOD

CROSS-REFERENCE TO RELATED APPLICATION

This is a continuation-in-part application of Ser. No. 626,034 filed June 29, 1984 for "BLOOD EXTRACTION AND REINFUSION FLOW CONTROL SYSTEM AND METHOD" by Paul R. Prince and Ronald L. Clark, now abandoned.

BACKGROUND OF THE INVENTION

1. Field of the Invention

This invention relates to a living subject adaptive blood flow control system and more particularly to a plasmapheresis blood flow control system which optimizes blood flow by limiting the blood flow rate in accordance with a flow control curve determined individually for each subject from actual subject data.

2. Discussion of the Prior Art

Plasmapheresis systems as well as other systems are known which require the extraction or reinfusion of bodily fluids from or to a living subject. The subject is typically a living human or animal subject but might also be a cadaver. In the case of a plasmapheresis system whole blood is extracted from the subject, plasma is separated from the whole blood, and an extraction product containing a higher concentration of blood cells than the whole blood is reinfused back to the subject while the separated plasma is retained and used for desired purposes. Frequently, a selected volume of saline solution is infused into the donor to replace the volume of plasma separated from the whole blood.

To optimize utilization of processing equipment and support personnel and minimize inconvenience and discomfort to the subject, it is desirable to remove or reinfuse bodily fluids as rapidly as possible. However, physiological restrictions on flow rates impose practical limitations on how fast pumping can proceed.

During extraction, if the pumping rate exceeds the flow capacity of a vein into which a phlebotomy needle is inserted, the intravenous pressure will drop below atmospheric pressure and the vein sidewalls will collapse under atmospheric pressure. When this collapsing vein problem occurs the blood pump must be stopped or significantly slowed until intravenous blood flow restores the intravenous pressure to a point greater than atmospheric pressure.

Oftentimes when the vein collapses about the needle the end of the needle will become occluded against the sidewall of the vein. When this happens the needle will frequently become embedded within the vein sidewall or will be sealed to the vein wall by virtue of the negative pressure within the needle and tubing that can be developed following a sudden occlusion. The needle then remains occluded even after the blood pump is fully stopped. It may even become necessary to remove and reposition the needle at the expense of considerable additional time delay.

Reinfusion presents a somewhat different flow rate problem from extraction. During reinfusion, if the pumping flow rate exceeds the vein flow capacity, the intravenous pressure increases until either the phlebotomy needle is forced out of the vein or the vein swells or even bursts or leaks into surrounding tissue. This creates an undesirable hematoma.

Predicting the optimum flow rate is difficult because it varies considerably from subject to subject. Even for a given subject the flow rate capacity can vary considerably over a period of time depending upon how vigorously flow stimulating exercises such as hand squeezing are being performed.

Attempting to optimize the blood flow rate by sensing flow path pressure adjacent the needle is uncertain because the pressure drop across the needle varies substantially with flow rate, hematocrit dependent blood viscosity and needle size parameters. It is therefore common to rely on a gravity driven flow rate far below the optimum or a pumping rate that is known to be well within the blood flow capacity of most subjects. This may be far below the optimum flow rate.

One arrangement in which a plasmapheresis system serves as a reservoir for receiving and returning bodily fluids is described in U.S. Pat. No. 4,086,924 to Latham, Jr. for "Plasmapheresis Apparatus". In this system extraction occurs under vein pressure and gravity. A multi-rate blood pump for the plasmapheresis system is accelerated or decelerated to match this flow rate. Reinfusion occurs at a predetermined rate with the blood pump set to a relatively low speed condition.

SUMMARY OF THE INVENTION

An individually adaptable bodily fluid flow control system for a plasmapheresis system in accordance with the invention controls fluid flow at an optimal rate for each different subject. The flow control system includes a non-invasive paristaltic fluid pump disposed to pump blood or other bodily fluids through a sterile flow path defined by disposable tubing connected between a phlebotomy needle or other donor attachment and a reservoir such as a plasma separation system. The system further includes a pressure sensor disposed to sense fluid pressure in the flow path between the needle and the pump, a controller coupled to control the pump flow rate in response to the sensed pressure and the actual pump operating speed, and a control panel coupled to convey operator commands to the controller.

The controller includes a programmed digital processor which operates for each new subject to determine zero flow vein pressure as well as sensed pressure at a test point flow rate which is selected to be well within the substantially linear flow rate capacity of the subject. To increase the zero flow vein pressure and thereby the dynamic range of operating internal vein pressures, a pressure cuff disposed near the needle and downstream of the vein blood flow direction may be used. The test point data is extrapolated to higher flow rates and translated by an amount less than the zero flow vein pressure to form a flow rate control curve. The controller then commands the fluid pump to maintain the system at a desired maximum nominal flow rate subject to any limitations imposed by the flow rate control curve. By using actual test point data the flow rate control curve can be individually adapted to the hematocrit dependent viscosity, tubing dependent pump flow constant, and needle characteristics encountered in each instance of use.

The digital processor operates on 50 msec cycles to periodically update pump flow rate commands to the pump. During each cycle the processor samples the sensed pressure, provides atmospheric calibration therefor and then provides lead lag compensation to generate a compensated pressure value. The actual flow rate is also calculated and updated in response to a pump motor velocity count signal and then used to find the pressure intersection point on the flow rate limit curve at the actual flow rate. The actual sensed pressure is subtracted from the curve intersection pressure point to produce a pressure error value.

The pressure error signal is then integrated and scaled to produce a flow control command. The integrator is subjected to a lower limit of zero, an upper limit equivalent to the maximum flow rate, and a rate of change limit to produce an adjusted flow control command which is applied as a flow rate command to a digital feedback flow rate control servo loop.

A forward portion of the servo loop includes a flow rate error integrater, a scaler and a D-A converter coupled to apply an integrated flow rate error signal to a pulse width modulated (pwm) motor control system which is itself a high bandwidth servo loop and drives the pump motor. A velocity signal from the pump motor is provided as feedback to the pwm motor control system and through a compensating lead lag circuit to provide the updated flow rate values which are used in accessing the flow rate limit curve and in determining the flow rate error signal in the flow rate servo loop. Actual flow rates and actual pressures contain scaling errors due to tubing geometry and hardness, and pressure sensor scale errors. However, since the system adapts by measuring a zero flow point and a second flow point with substantially the same scaling errors as are experienced at other flow rates and corresponding pressures, these errors are substantially eliminated, to the extent that the scaling errors are linear functions. That is, the system operates in its own flow and pressure units which are determined by the instant tubing and pressure sensor involved. First-order compensating corrections for pump or tubing nonlinearity is also provided for large negative pressures wherein the polyvinylchloride tubing, which has a relatively low hardness, tends to flatten somewhat within the paristaltic roller pump and therein exhibits a correspondingly somewhat reduced flow rate than that which is calculated from an ideal linear extrapolation of data measured at lower magnitude negative pressures.

BRIEF DESCRIPTION OF THE DRAWINGS

A better understanding of the invention can be had from a consideration of the following detailed description, taken in conjunction with the accompanying drawings in which.

DETAILED DESCRIPTION

Figure 1:
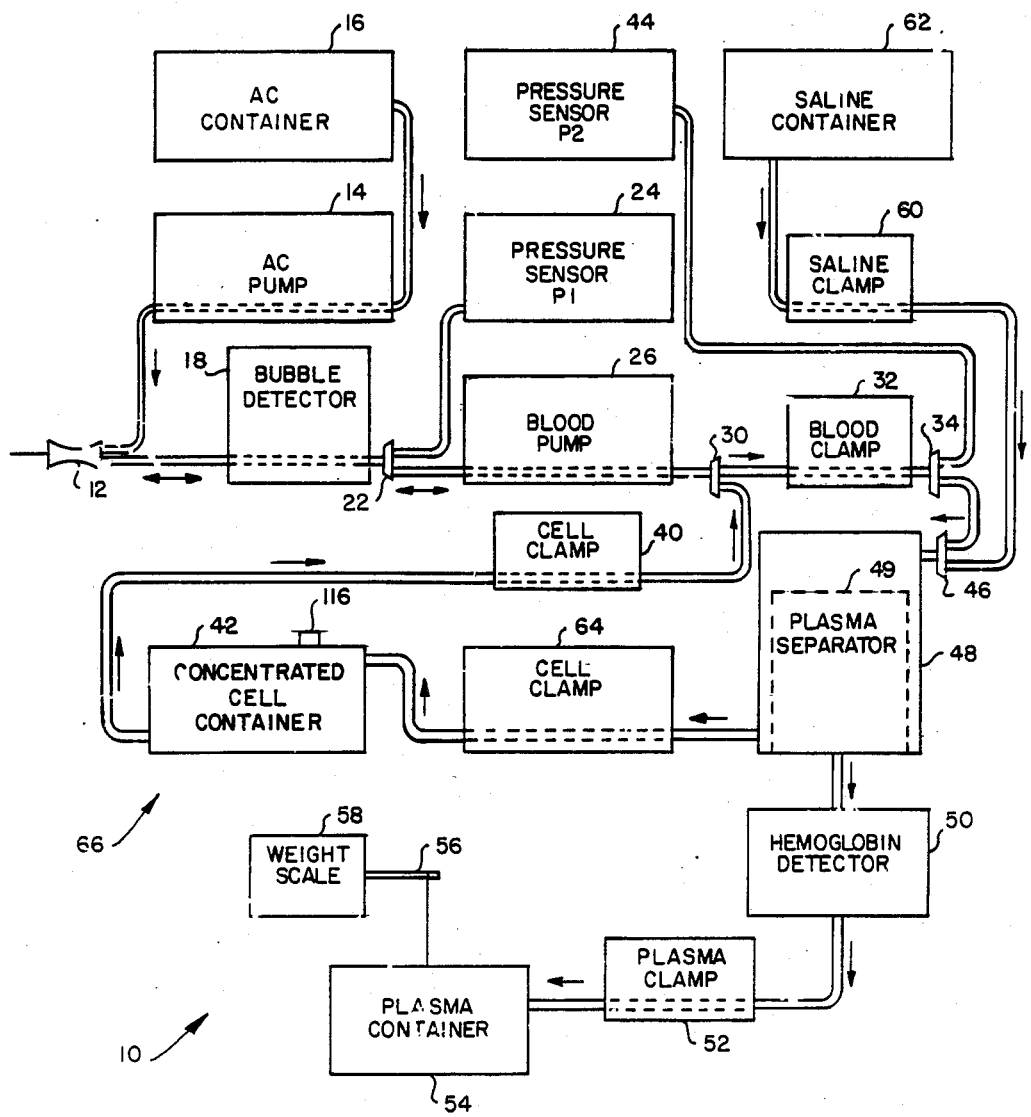
FIG. 1 is a schematic and block diagram representation of a fluid flow path for a plasmapheresis system using an adaptive body fluid flow control system in accordance with the invention.

Referring now to FIG. 1, there is illustrated a noninvasive, sterile plasmapheresis flow path 10 for a plasmapheresis system utilizing an adaptive bodily fluid flow control system in accordance with the invention. Intravenous connection of the flow path 10 to a subject is provided by a bodily fluid flow channel connection such as a phlebotomy needle 12 which is suitable for insertion into a vein of a living (or deceased) subject to provide bidirectional communication of blood and other fluids between the subject and the flow path 10 of the plasmapheresis system.

The flow path branches immediately adjacent the needle 12 with one branch extending through a noninvasive paristaltic anticoagulant pump 14 to an anticoagulant container 16. During a whole blood extraction cycle the anticoagulant pump 14 operates to supply and mix a small percentage of anticoagulant with the blood as it is being extracted to prevent activation of clotting mechanisms to prevent clinging of the blood to tubing sidewalls as it passes through the flow path 10. By mixing the anticoagulant with the whole blood at the needle 12 during extraction, the two fluids become fully mixed and less anticoagulant is required. This is a desirable effect which helps minimize the amount of anticoagulant in the separated plasma.

The other branch of the blood flow path 10 extends through a bubble detector 18 to another branch point 22. From branch point 22 one branch extends to a P1 pressure sensor 24 coupled to sense fluid pressure on the subject side of a blood pump 26. The pressure sensor 24 includes a disposable filter coupling the sensor to a pressure sensor tube 28 so as to maintain a noninvaded sterile atmosphere within the flow path 10. The second branch from branch point 22 extends through the noninvasive, paristaltic blood pump 26 to a branch point 30.

From branch point 30, one branch extends through a blood clamp 32 to another branch point 34. The other flow path at branch point 30 extends through a cell clamp 40 to the bottom of a concentrated cell container 42 which receives, and temporarily stores pending reinfusion, high hematocrit blood after a substantial portion of the plasma has been separated therefrom.

From branch point 34, one path extends to a second, P2 pressure sensor 44 while the other path extends through a branch point 46 to a plasma separator 48 which encloses a filter 49.

While the exact nature of the plasma separator 48 is not material to the present invention and can be fully conventional if desired, a highly advantageous plasma separator is a centrifugal filter type of separator as illustrated in application Ser. No. 591,925 filed Mar. 21, 1984 for "Method and Apparatus for Separation of Matter From Suspension" by Donald W. Schoendorfer. For this type of separator the end product plasma output is coupled through a hemoglobin detector 50 and a plasma clamp 52 to a plasma container 54 which is maintained at atmospheric pressure. The plasma container 54 is suspended from a tension arm 56 of a weight scale 58 which provides feedback to the plasmapheresis system of the amount of plasma within container 54. Since P2 pressure sensor 44 is coupled to the inlet of plasma separator 48 and since the plasma outlet of separator 48 is maintained at atmospheric pressure plus a small adjustment for vertical height differences, the pressure sensor P2 44 provides an indication of transmembrane pressure for the filter membrane within plasma separator 48. This transmembrane pressure indication can be useful in monitoring and controlling the operation of plasma separator 48.

Another flow path from branch point 46 extends through a saline clamp 60 to a saline container 62. This flow path enables the separator to be initially primed with a small amount of saline prior to initial use, to be cleansed with saline after final use, and provides a flow path of saline solution from the saline container 62 through branch point 46 to branch point 34 and then through blood clamp 32 to blood pump 26 and bubble detector 18 to phlebotomy needle 12. This path enables saline solution to be communicated to the subject at the end of a plasmapheresis operation to provide fluid replacement of any plasma removed from the whole blood of the subject.

A cell pump 64 is coupled between an outlet of plasma separator 48 on the same side of the membrane as the inlet at the top of concentrated cell container 42. Cell pump 64 thus controls the flow of high hematocrit blood from plasma separator 48 to concentrated cell container 42 where the high hematocrit blood is temporarily stored during an extraction subcycle. Whenever the concentrated cell container 42 becomes full, a reinfusion subcycle is executed in which cell clamp 40 is opened, blood clamp 32 is closed, and blood pump 26 is operated in the reverse direction to transfer the high hematocrit blood from concentrated cell container 42 back to the subject through bubble detector 18 and phlebotomy needle 12.

The entire bodily fluid flow path 10 including all of the branch points 22, 30, 34, 46 and the interconnecting tubing 66 are comprised of inexpensive, disposable materials which may be presterilized. Except for the plasma separator 48, the blood flow path is maintained completely noninvasive so as to protect against contamination and prevent and maintain sterility of the bodily fluids. The non-hardware portion of the flow path may be fully replaced for each different subject. Even the plasma separator 48 may be constructed such that only a sterile, disposable portion comes into contact with the bodily fluids. The risk of transmitting disease to the subject during the plasmapheresis operation is thereby minimized.

In order to optimize use of the plasmapheresis equipment and maintenance personnel while minimizing inconvenience and discomfort to the donor subject, it is desirable to proceed with a plasmapheresis operation as rapidly as possible. Typically, the factor which limits the plasmapheresis operating rate is the intravenous fluid flow rate for the subject donor. The present system is designed for operation at a nominal maximum flow rate of 100 milliliters per minute. Experience has shown that most donor subjects can supply and receive bodily fluids at or near this rate. However, a substantial portion cannot. The adaptive blood flow control system of the present invention is operable to determine the maximum available flow rate for either extraction or reinfusion and control blood pump 26 to operate either at the reduced maximum rate or at the nominal design flow rate of 100 milliliters per minute if the donor subject can handle the nominal flow rate.

A vein supplying or receiving intravenous bodily fluids through the phlebotomy needle 12 can be analogized to a small diameter, thin walled, rubber tube. Normally, the body maintains a pressure within the vein of approximately 6 mm. Hg. above atmospheric. This is sufficient to maintain the vein expanded and permit normal blood flow. However, if blood is extracted faster than it can be supplied by the vein, the pressure within the vein drops toward atmospheric, causing the external atmospheric pressure against the body to collapse the vein. Blood flow can be reinstated by terminating pumping through the needle until normal vein pressure is restored within the vein. However, frequently the sidewalls of the vein engage the end point of the phlebotomy needle as the vein collapses to thereby occlude blood flow through the needle. Even as the vein reexpands, the needle may remain occluded against the vein wall and it then becomes necessary to reposition the needle. This of course imposes considerable time delay and may cause donor anxiety.

During reinfusion care must also be taken to assure that the bodily fluid flow rate is not too great. If the flow rate is too great, pressure rises within the vein until the bodily fluids either begin to leak through the seal point between the needle and the vein sidewall or expand the vein until a break occurs. In either case, bodily fluids leak into the body tissue surrounding the vein to create an undesirable and even potentially dangerous hematoma.

During venepuncture it is common to place a pressure cuff around the upper portion of the subject's arm with a pressure of about 60 mm Hg to make the vein more visible. After venepuncture the pressure within the cuff is reduced to about 40 mm Hg during extraction and to substantially 0 during reinfusion. Thus, the 0 flow rate (through needle 12) internal vein pressure will be determined largely by the cuff pressure during extraction and will be approximately 40 mm Hg. The best way to optimize the extraction flow rate would no doubt be to sense actual internal vein pressure and limit flow rate to a magnitude at which actual vein pressure begins to approach atmospheric pressure. However, measurement of actual vein pressure is not practical without multiple needle procedures or expensive concentric dual needles. The present invention uses measurements at pressure-flow rate test points between the needle 12 and blood pump 26 to generate an estimate of what pressure the maximum flow rate will produce, based upon extrapolation of the measured curve for substantially linear pressure flow relationships and nonlinear pressure flow relationships when nearing saturation, i.e. pressure drop, due to subject flow limitations.

Figure 2:
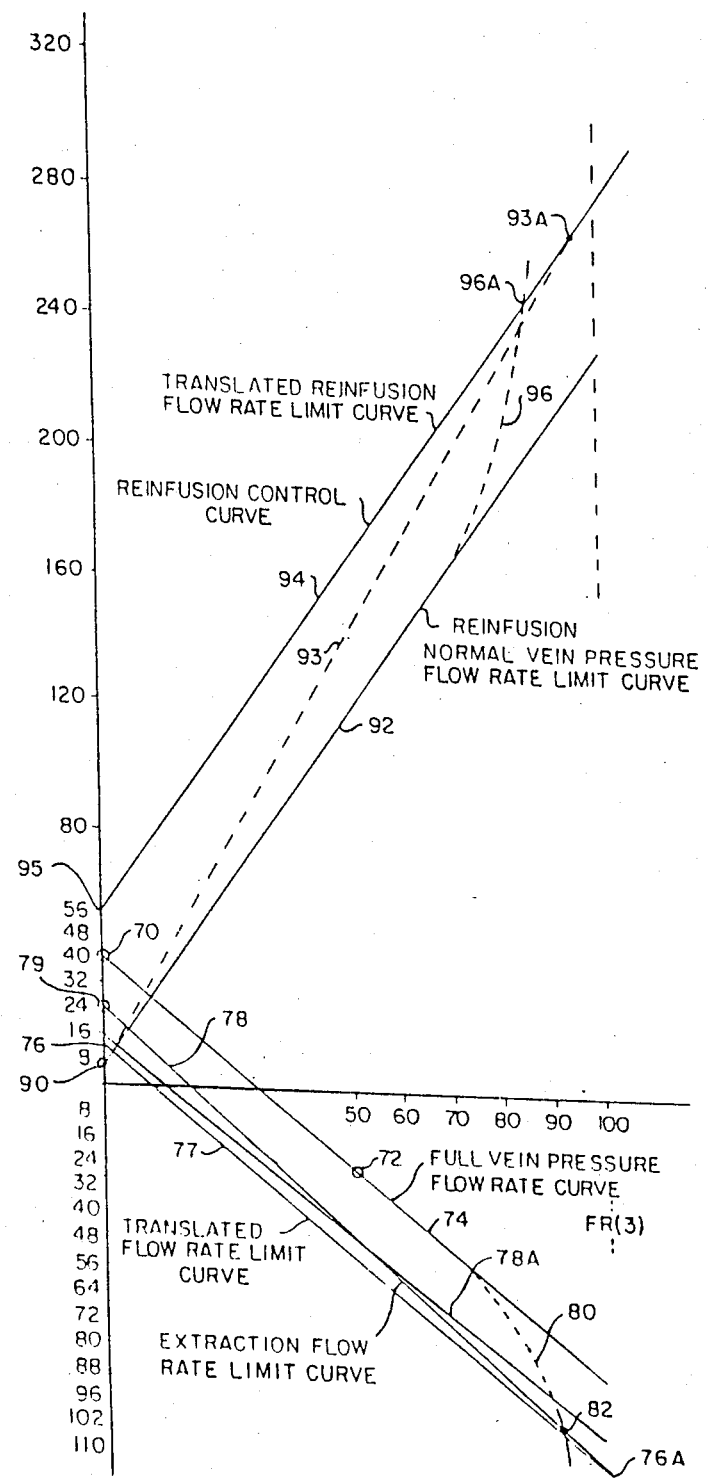
FIG. 2 is a graphical illustration of flow rate limit control curves for extraction and reinfusion.

Referring now to FIG. 2, in establishing the flow rate limit curve for extraction the adaptable flow rate control system samples the pressure at a 0 flow rate at point 70. With the pressure cuff inflated to a typical 40 mm Hg it would be expected that point 70 would also occur at approximately 40 mm Hg. For the second test point, the blood pump 26 is commanded to operate at a rate corresponding to 50 ml per minute, which is expected to be within the flow rate capability of virtually all donor subjects. In our present example the second test point occurs at a flow rate of 50 ml per minute and a pressure of −24 mm Hg relative to atmospheric pressure. If it is assumed that the donor subject is readily capable of providing the 50 ml per minute flow rate then the pressure difference between test point one at 70 and test point two at 72 is due to a loss induced pressure drop in the fluid flow path between the vein and the pressure sensor branch point 22. This pressure drop is due primarily to fluid flow through the constriction of the needle 12 which is dependent upon needle size, blood viscosity and flow rate. For a given plasmapheresis session the needle size parameters remain substantially constant and the pressure drop between the vein and the P1 sensor 24 is substantially proportional to fluid flow rate and viscosity. The adaptive flow control system takes advantage of this linear relationship by linearly extrapolating the pressure data from test points 70 and 72 at the beginning of each extraction subcycle, to generate a full vein pressure flow rate curve 74. The full pressure curve 74 is then translated downward by an amount equal to a difference in pressure between the 40 mm Hg pressure at 0 flow rate pressure at the first test point 70 and a minimum acceptable internal vein pressure such as 12 mm Hg at point 76 to generate a translated flow rate limit curve 77. The translated flow rate limit curve 77 thus has the general format of $$P=\{[P(2)-P(1)]/[FR(2)-FR(1)]\}\times FR+40-28,$$

where P is the instantaneous pressure, P(2) is the sensed pressure at test point 2, P(1) is the sensed pressure at test point 1, FR(2) is the flow rate at test point 2, FR(1) is the flow rate at test point 1, FR is the instantaneous flow rate, 40 is the zero flow rate sensed pressure intercept or full vein pressure and $-28$ is the maximum allowable intraveneous pressure drop within the vein to prevent vein collapse at any flow rate while providing 12 mm Hg of margin and may be given different values. The difference of $40-28=12$ produces an offset representing the minimum acceptable internal vein pressure with sufficient margin that the pressure cuff pressure could be lowered 8 to 10 mm Hg and still maintain a slight positive pressure within the vein.

The translated flow rate limit curve 77 can be rotated about its 100 ml per min. nominal flow rate intercept point at 76A into a final extraction flow rate limit curve 78 by increasing the translated zero flow limit point 76 by a zero flow added margin from point 76 at 12 mm Hg to point 79 at 24 mm Hg. This provides two advantages over curve 77. It provides even further margin against vein collapse at low flow rates for subject donors of low blood flow capability and it forces the vein to reach a substantial fullness prior to startup since flow is then not allowed to begin for pressures below 24 mm Hg at zero flow.

The extraction flow rate curve 78 thus has the general format of $$P=\{[P(2)-P(1)]/[FR(2)-FR(1)]-12/FR(3)\}\times FR+40-28+12$$

where the $+12$ corresponds to the zero flow added margin which may be given different values and the $-12/FR(3)$ corresponds to the increase in slope to cause the flow rate curve to match the translated flow rate curve 77 at the maximum design flow rate FR(3). The other parameters remain as defined for translated flow rate limit curve 77.

An alternative procedure for generating an alternative extraction flow rate curve 78A has been found to be advantageous for low flow rate subjects such as older subjects or subjects with small veins. It has been found that such subjects are more likely to experience an occlusion at a high flow rate than at a low flow rate.

By in effect rotating the alternative extraction flow rate curve 78A counterclockwise relative to the full vein pressure flow rate curve 74, somewhat faster flow rates are produced when the actual flow rates are quite low and somewhat slower flow rates are produced when the actual flow rates approach the 100 ml per min. maximum rate. This counterclockwise rotation also has the effect of producing a greater pressure error signal under normal startup conditions. This greater pressure error signal causes the blood pump 26 to accelerate more rapidly and hence reach the steady state operating point more quickly.

A practical technique for simultaneously translating and rotating the full vein pressure flow rate curve 72 to produce the alternative extraction flow rate curve 78A is to define curve 78A by two points. The first point is determined by subtracting a first fixed value from the zero flow rate test pressure at test point 70. For example a first fixed value of 24 is subtracted from the zero flow test point 70 pressure of 40 mm Hg to produce a pressure value of 16 mm Hg at zero flow. The second point is determined by subtracting the first fixed value from the projected pressure at the 100 ml per min upper flow-rate limit and then adding a second fixed value to the difference. For example, subtracting 24 from $-88$ mm Hg leaves an intermediate value of $-112$ mm Hg. A second value of 8 mm Hg might then be added to $-112$ to produce a second point at a pressure of $-104$ and a flow rate of 100 ml per min. These first and second points can then be used to define the line representing the alternative extraction flow rate curve 78A. The alternative extraction flow rate limit curve 78A is thus both translated downward and rotated counterclockwise relative to the full vein pressure flow curve 72.

As measured at P1 pressure sensor 24 the actual sensed pressure will follow a curve 80 which will substantially follow flow rate curve 74 so long as the donor subject is able to supply the amount of blood being withdrawn. However, as the amount of blood withdrawn approaches the maximum accommodation rate, the internal vein pressure will begin to drop and this pressure drop will be superimposed upon the pressure drop across the needle so that actual flow rate curve 80 will begin to decrease in pressure more rapidly than flow rate curve 74. The adaptive blood flow control system uses P1 pressure sensor 24 to monitor the actual pressure of flow rate curve 80 and when curve 80 crosses extraction flow rate limit curve 78 at point 82 further increases in blood flow rate are inhibited. The adaptive blood flow control system then operates to maintain system operation at the point at which actual flow rate curve 80 crosses extraction flow rate limit curve 78 so long as this crossover point 82 is less than the nominal design flow rate of 100 ml per minute. The maximum nominal flow rate of 100 ml per minute will be pumped so long as the donor subject is able to accommodate this nominal design rate.

A reinfusion flow rate limit curve can be determined for reinfusion in substantially the same manner as for extraction. Pressure can be sensed at first and second flow rate of test points, for example a first test point 90 at a flow rate of 0 and a second test point at a flow rate which is considered to be well within the return flow rate accommodation of any donor subject. Because the pressure cuff is depressurized for reinfusion, the 0 flow rate ordinate intercept test point 90 will normally be at approximately 6-8 mm Hg, which is the normal intravenous blood pressure.

A preferred method of return cell flow control assumes a predetermined approximate increase in viscosity due to the removal of plasma, such as a doubling of viscosity. The slope of the predetermined viscous pressure drop curve found for extraction is therefore increased by multiplying by a factor of 1.0 to 3.0 (1.5 being presently preferred) and its sign is changed to provide the reinfusion pressure control curve slope. The vein characteristics on reinfusion are tolerant of small overpressures, unlike extraction under pressure which causes vein collapse. Therefore a significant positive offset at zero flow is allowable, such as 48 mm Hg.

The needle-concentrated cell flow relationship can then be represented by normal vein pressure flow rate curve 92 of FIG. 2 wherein point 90 is the zero flow vein pressure without pressure cuff. In this example the slope of full vein pressure flow rate curve 72 is multiplied by −2 to obtain the slope of reinfusion normal vein pressure flow rate limit curve 92. Translating flow rate limit curve 92 upward by 48 mm Hg produces a translated flow rate limit curve 94 having a 56 mm Hg zero flow rate intercept at point 95. Translated flow rate limit curve 94 becomes the final reinfusion control curve to limit the actual pumping rate. The summing point 95 on translated control curve 94 is the result of offsetting positively by 48 mm Hg, changing the sign of, and increasing the slope of curve 74 by a factor of two.

A curve 93 represents actual sensed pressure in a hypothetical case wherein the concentrated cells are sufficiently viscous to cause somewhat reduced flow at the stabilizing intersection point 93A with curve 94. This reduced flow can be a benefit since for excessively high flow rates of highly viscous fluids, the fluid shear may become excessive and damaging to red blood cells.

This method of generating a reinfusion control curve from the extraction curve 74 has the added advantage that the blood pump is not required to pause for an intermediate measurement since the needle and source blood characteristics are determined in the extraction measurement. If the incoming blood from the subject is of relatively low hematocrit, such as 30, the control curve 94 slope will be relatively small, and the 48 mm offset will allow the return cell hematocrit (and therefore viscosity) to be substantially increased over the incoming blood hematocrit while continuing to allow high flow rates. But for relatively high hematocrit incoming blood, such as 45, the control curve 94 slope will be relatively steep so that the 48 mm offset will be relatively insignificant and not allow much more than a doubling of viscosity without a reduction in return flow rate to save the return cells from exposure to excessive shear.

Curve 96 of FIG. 2 illustrates a hypothetical actual flow pressure curve having a nonlinearity which would occur if return flow restriction occurs or if the needle slipped into the flesh and a free return flow was inhibited. This situation would normally cause the potential of a hematoma formation. The intersection of curve 96 with curve 94 at point 96A reduces return cell flow to accommodate reduced flow capacity. Rapid increases in pressure beyond curve 94 cause total pump shutdown.

Control curve 94 for reinfusion of concentrated cells thus has the general formula $$P = M\{[P(1) - P(2)]/[FR(2) - FR(1)]\} \times FR + 48 + 8$$

wherein M is a positive viscosity multiplying term applied to the negative of the extraction slope, and may take on other values, the +6 is the measured zero flow vein pressure, and the 48 is an offset from the measured zero flow vein pressure and may be assigned different values. The change in the sign of the slope is effected by subtracting P(2) from P(1) instead of P(1) from P(2) to reduce processing time.

The hypothetical actual donor subject concentrated cell flow rate curve represented for example by dashed line curve 93 illustrates the system flow rate limit function for reinfusion. The adaptive blood flow control system operates to reinfuse blood at as fast a rate as possible up to a limit of the flow rate point at which the actual sensed pressure represented by curve 93 intercepts the flow rate limit curve 94 or until the nominal design flow rate of 100 ml per minute is reached, whichever is less. The limit of 100 could be higher or lower values and could reasonably be as high as 130 mm Hg. The system thus assures that the optimum flow rate is attained whether for extraction or reinfusion.

Figure 3:
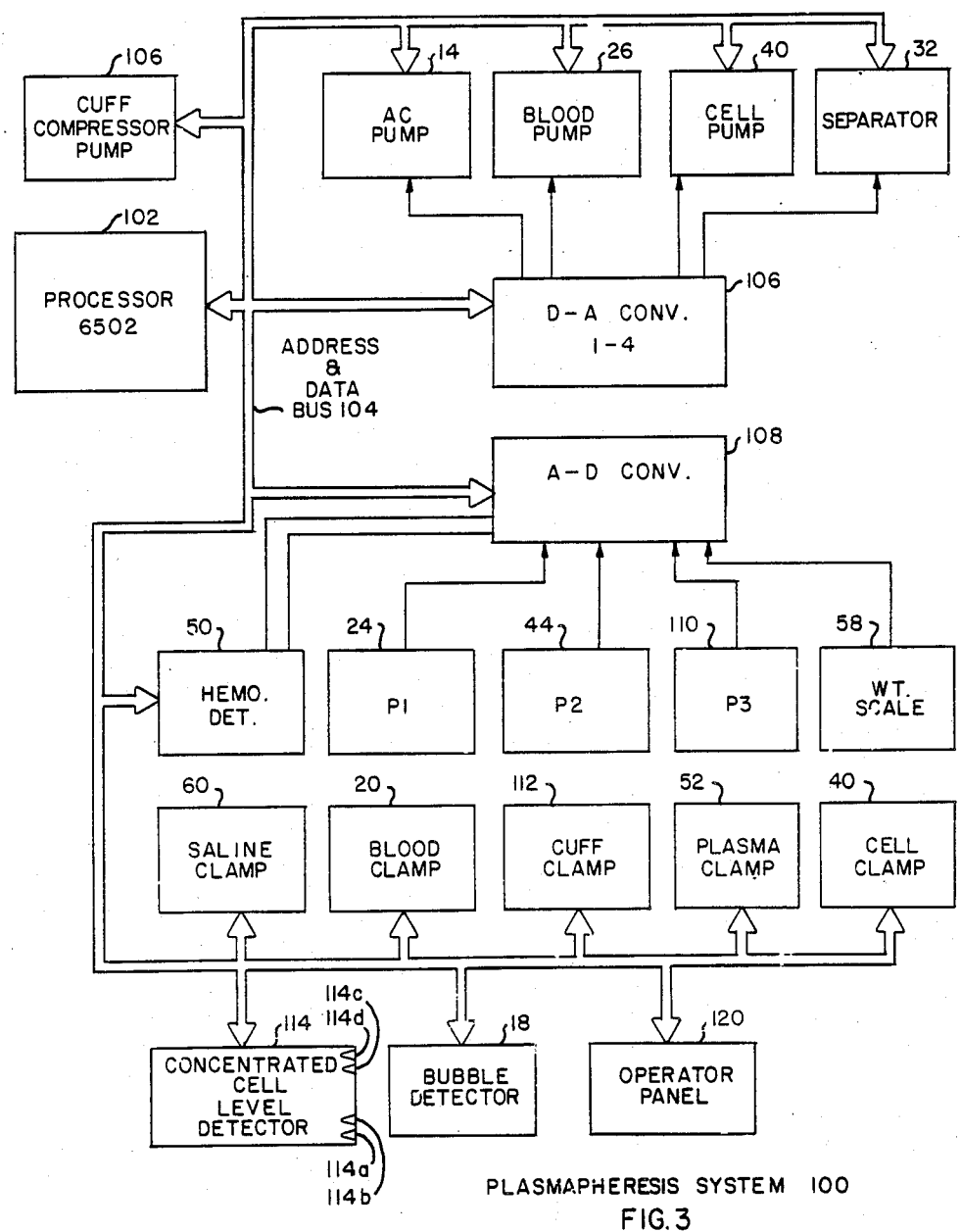
FIG. 3 is a functional block diagram representation of a plasmapheresis system incorporating an adaptive blood flow control system in accordance with the invention.

Referring now to FIG. 3, plasmapheresis system 100 includes a data processor 102 which maintains operational control over plasmapheresis system 100. In the present example processing 102 is a 6502 type of microprocessor and is deemed to include all of the memory and peripheral logic which is typically associated with a microprocessor to provide proper system operation. Processor 102 communicates with other portions of plasmapheresis system 100 through an address and data bus 104. Among the items coupled to address and data bus 104 is a cuff pressure pump 106. Cuff compressor pump 106 controls the pressure within the arm cuff which is utilized to increase intravenous pressure in a subject donor.

Also connected to memory bus 104 are the three fluid pumps, anticoagulant pump 14, blood pump 26, and cell pump 40, and the plasma separator 32. The commercially available motors driving the rotating portions of these devices each include Hall effect sensors which generate 12 position increment signals per motor revolution. These position feedback signals are accumulated by a resetable counter associated with each of the motors with the accumulated counts being periodically provided as position and velocity feedback over memory bus 104 to processor 102. A digital-to-analog converter 106 is also coupled to memory bus 104 to receive velocity commands from processor 102 for each of the motors associated with AC pump 14, blood pump 26, cell pump 40 and separator 32. Digital velocity commands received from processor 102 are converted to analog signals which are communicated to the respective motors.

An analog-to-digital converter 108 is connected for communication with processor 102 over memory bus 104. Analog-to-digital converter 108 receives analog information over up to 8 channels and conveys the information in digital form to processor 102. Among the devices providing analog signals to analog-to-digital converter 108 are the hemaglobin detector 50 which provides two channels of analog optical information which is sensitive to the appearance of red hemaglobin within the plasma, pressure sensor P1, pressure sensor P2, and a third pressure sensor P3 110 which is responsive to the pressure within the pressure cuff attached to the donor subject's arm. Each of the pressure sensors provides a single channel of input to analog-to-digital converter 108. Weight scale 58 provides another single channel of analog input to converter 108 to indicate the weight of the plasma and bag hanging from force arm 56 of weight scale 58. Each of the noninvasive fluid flow clamps, including saline clamp 60, blood clamp 20, plasma clamp 52 and cell clamp 40, are coupled to receive digital clamping commands over memory bus 104 and respond thereto by opening or closing the flow path through the clamp in response to the received commands. Also coupled in a similar manner is a cuff clamp 112 which is disposed to selectively maintain or relieve air pressure within the pressure cuff attached to a donor subject's arm.

A concentrated cell level detector 114 is also coupled to communicate over memory bus 104 digital signals indicating the level of concentrated cells within concentrated cell container 42. In the present example the concentrated cell level detector 114 includes four optical sensors disposed to indicate whether or not the concentrated cell fluid is above or below a bottom sensor 114a disposed near the bottom of the concentrated cell container 42, above or below a next to bottom sensor 114b disposed a short distance above the bottom sensor 114a, above or below a top sensor 114d disposed near the top of concentrated cell container 42 to indicate a full condition, or above or below a next to top sensor 114c disposed a short distance below the top sensor 114d to indicate an almost full condition.

Bubble detector 18 is digitally coupled through memory bus 104 to processor 102 to provide an indication of any emergency condition in which a bubble is detected in the intravenous fluid flow line near the phlebotomy needle.

An operator panel 120 is also coupled over address and data bus 104 to processor 102. Operator panel 120 receives numeric commands as well as advance and stop or back commands to control the stepping of the operator through the various steps associated with plasmapheresis. The operator panel 114 also provides feedback information to the operator in the form of a display which indicates the status of the plasmapheresis operation.

Figure 4:
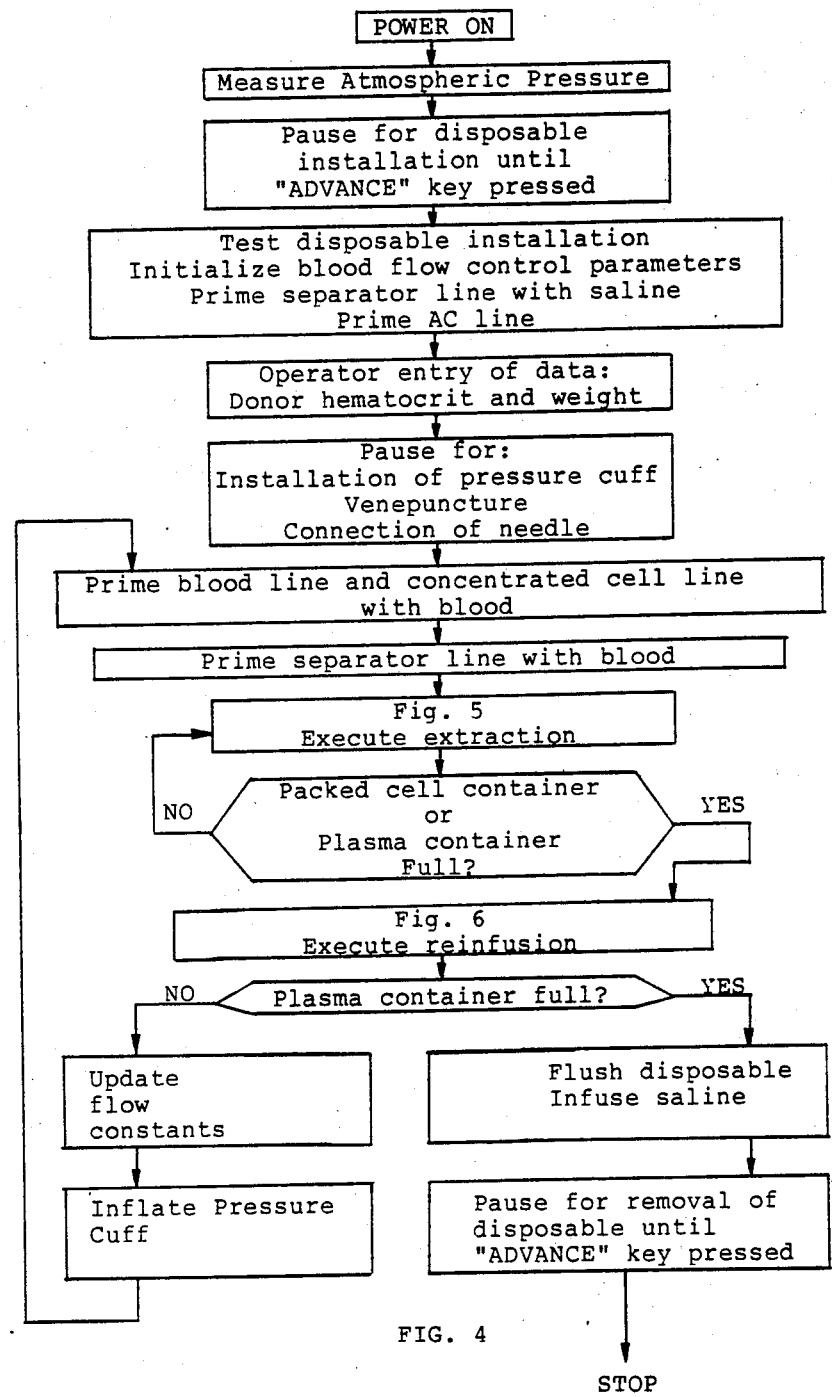
FIG. 4 is a flow chart illustrating a plasmapheresis operation.

A typical plasmapheresis operating cycle utilizing plasmapheresis system 100 is illustrated in FIG. 4. Following power turn-on or completion of a prior cycle, the system 10 uses P1 pressure sensor 24 to measure atmospheric pressure for use in calculating sensed pressure differences relative to atmospheric pressure. System 10 then pauses for installation of the disposable tubing, pressure snsor interfaces, plasma container 54, concentrated cell container 42 and separator filter 49 which form sterile, the noninvasive fluid flow path shown in FIG. 1.

Upon completion of installation of the disposable apparatus the operator presses the ADVANCE key and the plasmapheresis system 100 progresses to a test and initialization step.

In the test and initialization step the system 100 uses the various pumps and clamps to pressurize the disposable tubing and test for any leaks. If any leaks are found the system stops and invites the operator to correct them through a display message. Assuming no leaks are found the system opens the saline clamp 60 for a short, predetermined period of time to allow the gravity feed saline prime of the tubing leading to plasma separator 48 as well as a small space within plasma separator 48 between the peripheral wall and the filter membrane 49. During this procedure cell pump 64 is operated to draw air and eventually a small amount of saline solution from plasma separator 48 to concentrated cell container 42 where the air may be exited through a filtered vent aperture 116. Upon completion of the saline prime the anticoagulant pump 14 is operated to prime the tubing between anticoagulant container 16 and phlebotomy needle 12 with a predetermined volume of anticoagulant fluid.

Upon completion of the anticoagulant prime the system pauses and the display invites the operator to enter donor subject related information defining hematocrit and weight for the specific donor if known. Additional optional information may be entered at this time if desired. The optional information can include a desired anticoagulant to blood ratio and a percentage of plasma or yield to be taken from the blood. If the operator enters no values predetermined default values are used.

The optional parameters may also include an operator selected maximum flow rate value less than the system maximum flow rate value of 100 ml/min. If the donor subject has a past history or some physical condition suggesting that the maximum flow rate should be reduced, this value can be entered at this time. The reduced maximum value may preclude the occurrence of an occlusion as the flow rate accelerates toward the default maximum value of 100 ml per min.

The data processor 102 stores and maintains three different flow rate limit values. The first is an absolute limit that is defined to be 100 ml per min at the time of manufacture and cannot be changed under ordinary circumstances. The second is the operator selected maximum flow rate value, which is constrained by system design to be between 60 and 00 ml per min. A default value of 100 ml per min is used if the operator does not enter a different value.

The third or current flow rate limit value actually defines the flow rate limit which is controlling at any given time during the operation of the plasmapheresis system. The current flow rate limit value may be automatically adjusted from time to time but is always constrained to be less than or equal to the operator selected maximum flow rate value. Any time the operator selected maximum flow rate value is updated by an operator the current flow rate value is set to a matching value.

The operator may adjust the operator selected maximum flow rate value at any time during system operation by actuating a key on operator panel 120. The operator is then presented with a menu of available functions which include updating of the operator selected maximum flow rate value. If this option is selected the operator is prompted to enter the new value. In the present design fluid flow through path 10 is automatically and quickly stopped whenever an operator requests a selection menu. Operation resumes under control of any new parameters upon completion of any operator selections. However, it would be feasible to continue system operation during operator selections (after the initial start-up procedure) and adjust system operation to any operator selections as they are made.

The current maximum flow rate value may also be automatically adjusted during system operation. If pressure sensor P1 24 suggests that an occlusion has occurred, fluid flow in path 10 is rapidly stopped and the current maximum flow rate value is reduced by a predetermined value such as 10. If the occlusion is not permanent, sensed pressure will quickly begin to rise and normal operation will resume with the lower current maximum flow rate value controlling the flow rate limit. If a complete extraction cycle is completed without an occurrence of an occlusion, then the current maximum flow rate value is increased by a predetermined value such as five, but is not permitted to exceed the operator selected flow rate value.

It should be appreciated that the current maximum flow rate value is an upper limit which is superimposed upon flow rate commands that are determined using the flow rate limit curves as discussed in conjunction with FIG. 2. If the determined flow rate is below the current maximum flow rate value, then the current maximum flow rate value has no effect upon system operation.

As noted previously, the operator may update the operator selected maximum flow rate value at any time but would normally do so during the pause for operator information that occurs during the system start-up procedure.

Upon entry of this information, the system pauses and invites the operator to install the pressure cuff. Upon installation of the pressure cuff the system proceeds with prompts for venepuncture and connection of the blood and AC tubing to the phlebotomy needle 12. The operator then actuates the ADVANCE key and the system proceeds to a blood prime operation step.

During blood priming the system first senses the intravenous pressure at a 0 flow rate to establish test point 1 data and then proceeds to prime at 50 ml per second while sensing pressure to derive test point 2 data. The system 100 first operates to prime the concentrated cell path through bubble detector 18, blood pump 26, and cell clamp 40 to concentrated cell container 42 until the fluid level in concentrated cell container 42 reaches the bottom sensor 114a. Blood clamp 32 is closed at this time. After the initial prime and following each reinfusion cycle a full prime is not required and a predetermined amount of blood of approximately 10 cc is pumped to clear the blood line between phlebotomy needle 12 and branch point 30 of concentrated cells so that they are not pumped to the separator 48.

Then cell clamp 40 closes, blood clamp 32 opens and the blood prime continues for the separator line with blood pump 26 pumping blood through bubble detector 18, pump 26, branch point 30, blood clamp 32, branch point 34, and branch point 46 to plasma separator 48. While the blood pump 26 is running cell pump 64 operates at substantially the same speed to extract the fluid from plasma separator 48 and pump it into concentrated cell container 116 while the fluid is replaced by blood. During the initial prime the replaced fluid is primarily saline solution from the saline prime. After each reinfusion subcycle the fluid is primarily blood. If a rotating filter is used, the filter is accelerated to normal speed during this time. Priming continues until the concentrated cell container reaches the next to bottom indicator 114b.

As soon as concentrated cell container 42 is filled with priming fluids to the next to bottom indicator 114b the plasma clamp 52 is opened to begin the plasma separation operation and blood pump 26 is energized to produce the optimum flow rate as discussed in conjunction with FIG. 2. During the extraction cycle plasma separator 48 separates plasma from the whole blood with the plasma passing through hemaglobin detector 50 and plasma clamp 52 to plasma container 54. The remaining high density concentrated cell fluid passes from plasma separator 48 through cell pump 64 to concentrated cell container 42 under control of the cell pump 64. The plasma side of plasma separator 48 is maintained at atmospheric pressure because the plasma flows into a soft walled plasma container 54 which is subjected to atmospheric pressure. The pressure sensor 44 coupled to the inlet of plasma separator 48 through branch point 34 and branch point 46 thus indicates the transmembrane pressure for the separator filter membrane 49 within plasma separator 48.

During execution of the extraction cycle processor 102 operates to update system 100 status parameters every 50 msec. These status parameters include pressure sensor values, motor rotational counts, clamp status, fluid level indications, and status of the bubble detector 18 and operator panel 114. So long as neither the concentrated cell container 42 is indicated as being full by the concentrated cell level detector 114 nor the plasma container is indicated as being full by weight scale 58 the extraction cycle continues.

Initially, the system 100 uses a predetermined default value for flow constants defining the ratio of flow volume to rotational count for the blood pump 26 and cell pump 64. However, to achieve improved accuracy these flow constants are updated using actual volume data during each extraction-reinfusion cycle. Rotational counts (12 per revolution) are maintained while the fluid level in concentrated cell container 42 rises from sensor 114b to 114c. The weight of plasma container 54 is also stored for these points so that the corresponding volume change can be added to the known volume change in concentrated cell container 42 to get the total volume flow through blood pump 26. The extraction direction flow constant is similarly determined for blood pump 26 during each extraction part cycle. The new flow constants are then substituted for the old ones just before the blood line is primed for the second and each subsequent cycle.

When one of the fluid containers is detected as full, the system proceeds to execute a reinfusion cycle during which concentrated cells within concentrated cell container 116 are returned to the donor until the fluid level in concentrated cell container 42 reaches the bottom level indicator point 114a. After the concentrated cell container 42 is indicated as empty by concentrated cell level detector 114, the status of the plasma container 54 is tested. If it is not full the blood line is reprimed with blood and the next extraction cycle is executed as before.

If, following a reinfusion cycle the plasma container 54 is found to be full, the blood and concentrated cell fluid flow paths are flushed with saline as the blood and concentrated cell fluids flushed from the flow paths are returned to the donor subject in a reinfusion operation. Typically, the final reinfusion of saline solution continues until a selected quantity of saline solution sufficient to flush the plasma separator 48 and flow path from plasma separator 48 through concentrated cell container 42 and blood pump 26 has been flushed with saline solution. Then, cell clamp 40 is closed, separator clamp 32 is opened and flushing of saline solution from container 62 continues through branch point 46, branch point 34 and branch point 30 to the needle 12 under control of blood pump 26. Pumping of saline solution typically continues until a quantity of saline solution equal to the amount of plasma that has been removed from the subject donor is infused into the subject donor. The system 100 then pauses for removal of the used disposables, and installation of new disposable apparatus pending activation of the advance key to begin a new plasmapheresis operation with a new donor subject.

Figure 5:
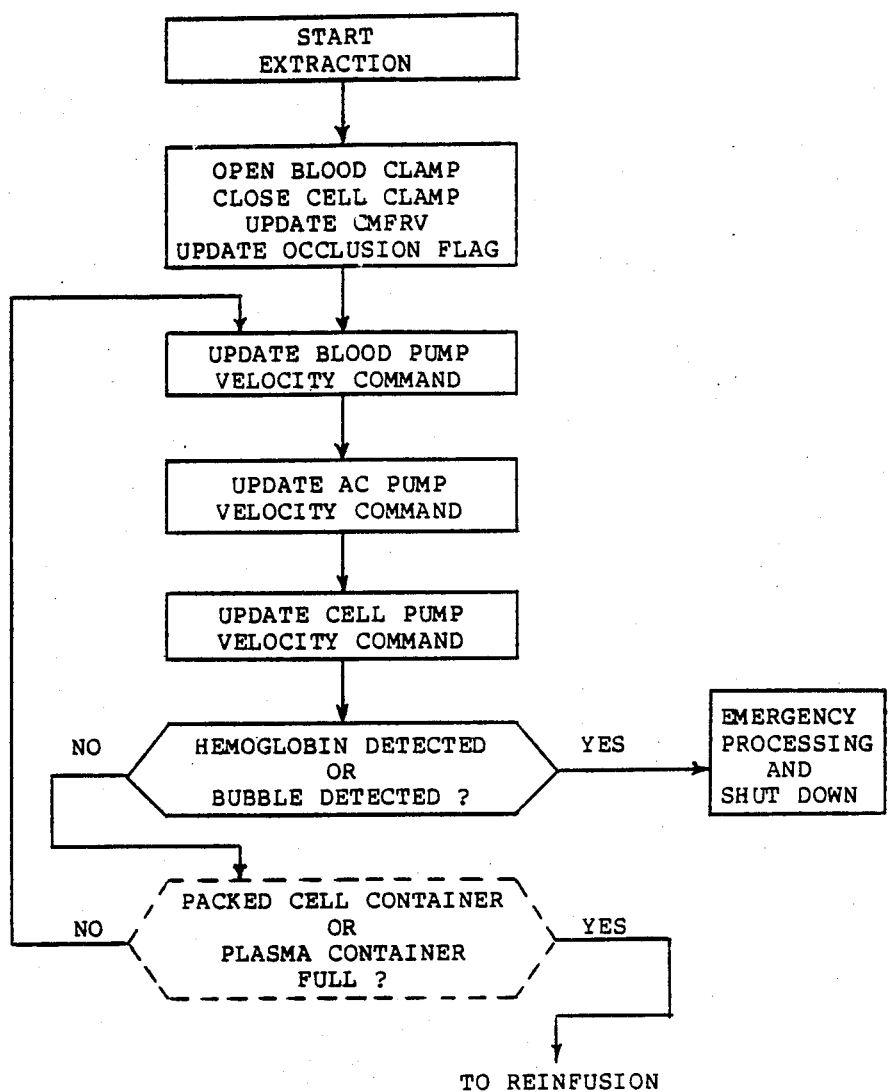
FIG. 5 is a flow chart illustrating in greater detail an extraction step used in the operation illustrated in FIG. 4.

A flow chart illustrating the execute extraction step shown in FIG. 4 is illustrated in greater detail in FIG. 5, to which reference is now made. Preliminarily the blood clamp is opened, the cell clamp is closed, and an occlusion flag update occurs. An occlusion flag is set whenever an occlusion is detected during an extraction cycle. If the occlusion flag is reset then no occlusion occurred during the preceding extraction cycle. The maximum flow rate is therefore increased by increasing the current maximums flow rate limit valve by a selected amount such as 5 ml per min, but not above the operator selected maximum flow rate value. If the flag is set, it is now reset so that it will indicate an occlusion free extraction cycle unless it is again set during the current extraction cycle. This automatic adjustment of the current maximum flow rate valve allows the system to automatically adjust the flow rate limit toward the maximum occlusion free flow rate. The 50 msec extraction update cycle begins with an updating of blood pump and velocity commands as well as other commands for system operation not directly related to the blood flow control. This update cycle includes the acquisition of system status data and calculation of new command parameters. Also directly related to the blood flow control during extraction is the updating of the anticoagulant pump velocity command and the updating of the cell pump velocity command. Processor 102 then looks at the acquired data from hemoglobin detector 50 and bubble detector 18. If either hemoglobin or a bubble are detected or any of the status parameters such as pressure are outside an acceptable range an emergency message is displayed and the system is shut down as part of an emergency processing operation.

Normally the hemoglobin and bubble tests will be negative and the processor 102 will test to see if either the packed cell level detector 114 indicates a full condition or the weight scale 58 indicates a full condition for the plasma container 54. If either container is indicated as being full the flow chart branches to a reinfusion cycle. Otherwise, the extraction update cycle is reexecuted.

Figure 6:
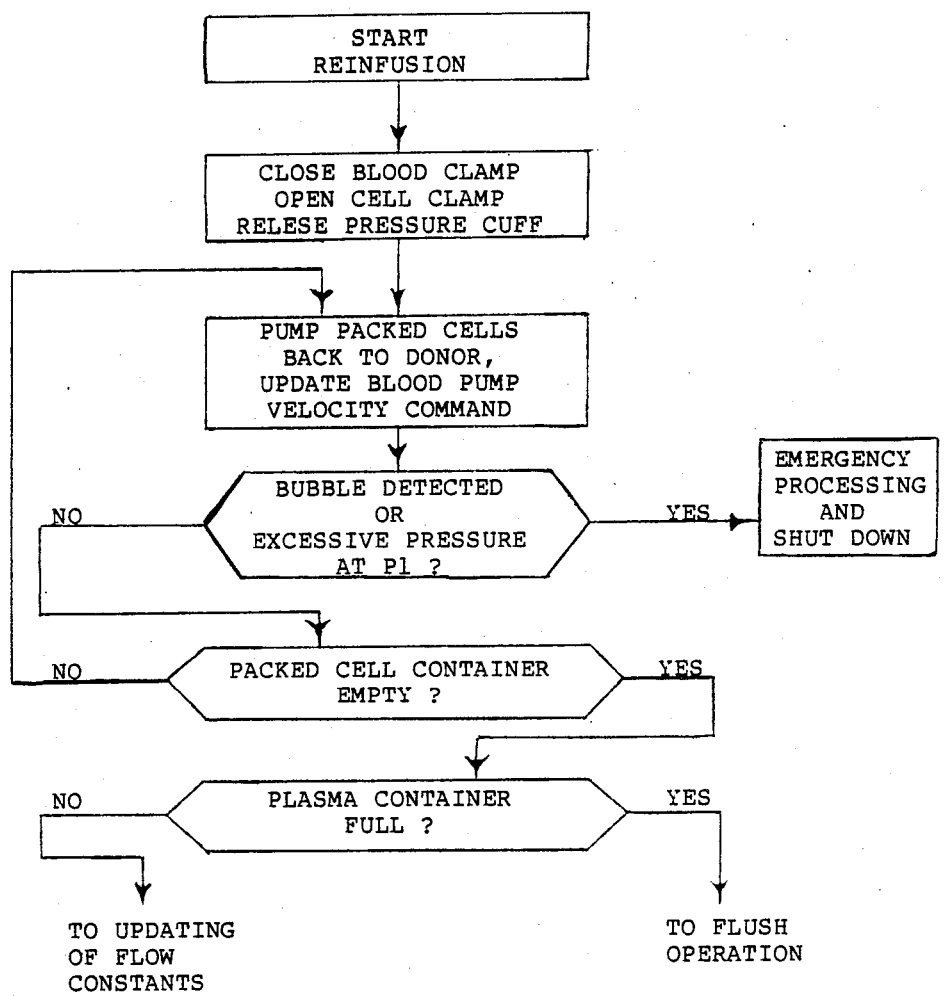
FIG. 6 is a flow chart illustrating in greater detail a reinfusion step used in the operation illustrated in FIG. 4.

The reinfusion cycle of FIG. 4 is illustrated in greater detail in the flow chart of FIG. 6 to which reference is now made. At the start of reinfusion the blood clamp 20 is closed, cell clamp 40 is opened and cuff clamp 112 is open to release pressure in the pressure cuff. The system then proceeds to pump packed cells back to the donor subject, with the blood pump velocity command being updated on a 50 msec cycle as was the case during extraction. However, during reinfusion the translated reinfusion flow rate limit curve 94 is utilized as shown in FIG. 2 rather than the extraction flow rate limit curve 78 which is used for extraction.

During reinfusion a test is then made for sensing of bubbles by bubble detector 18 and excessive pressure at P1. The sensing of pressure by P1 pressure sensor 24 at this point is an extra limit test over and above the normal flow rate update which occurs in conjunction with the flow rate calculation of flow rate control parameters. If a bubble is detected or the pressure at P1 is above the predetermined limit, emergency processing begins with the display of an emergency message and the system 100 is shut down with all pumps being rapidly stopped. Normally the system will not detect a bubble or excessive pressure and it will then test the level indication data from concentrated cell level detector 114. If concentrated cell container 42 is not empty, the cycle repeats. However, if the concentrated cell container is indicated as being empty, a test is made as to whether or not the plasma container is full. If the plasma container is full the operation of system 100 proceeds to flush the disposables as indicated in FIG. 4. If plasma container 54 is not full, then the system proceeds to a new extraction cycle after updating the pump flow constants and reinflating the pressure cuff.

Figure 7:
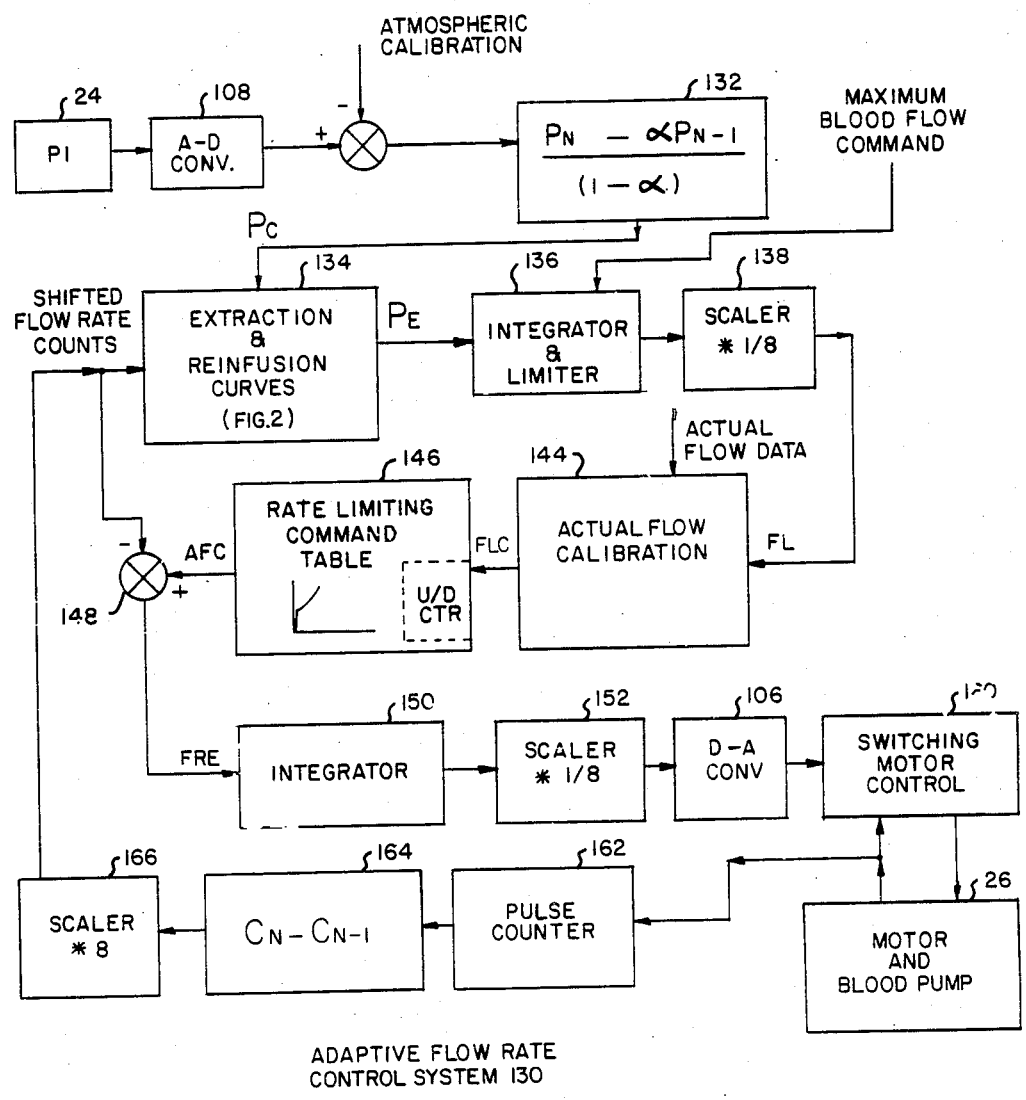
FIG. 7 is a functional block diagram representation of a flow rate control update cycle for the adaptive flow rate control system.

An adaptive flow rate control system 130 controlling the operation of a motor M2 driving blood pump 26 is illustrated in functional block diagram form in FIG. 7, to which reference is now made. While not shown explicitly, it will be appreciated that the digital mathematical operations are executed by processor 102 (FIG. 3). In general, the adaptive control system 130 responds to pressure indications from P1 pressure sensor 24 and actual motor velocity count signals from motor M2 for blood pump 26 to generate motor velocity command signals for motor M2 and blood pump 26.

The operation of motor M1 driving AC pump 14 and motor M3 driving cell pump 40 are scaled relative to motor M2 driving blood pump 26. For example, AC pump 14 might pump 1 to 5 percent of the volume of blood pump 26 while cell pump 40 pumps 50% of the volume of blood pump 26. Except for the velocity scaling, the velocity control systems for the motors driving AC pump 111 and cell pump 40 are essentially the same as system 130 and are therefore not separately shown.

Pressure indications received from P1 pressure sensor 24 are converted to digital form by analog-to-digital converter 108 and communicated to processor 102. The digital pressure values are calibrated to place a zero pressure indication at atmospheric pressure by subtracting an atmospheric calibration factor. The calibrated pressure is then subjected to a lead lag compensation function in the form $$P_c = [P_n - \alpha P_{n-1}]/[1-\alpha].$$

where $P_n$ is the current calibrated pressure indication, $P_{n-1}$ is the lead lag compensated pressure indication from the preceding update cycle, and $P_c$ is the resulting compensated pressure indication. It will be recalled that during operation of blood pump 26 the motor M2 velocity command is updated repetitively on a 50 msec cycle. $\alpha$ is a proportioning constant which might typically be about 0.5. The lead lag compensation of the calibrated pressure indication is represented by a block 132 and tends to compensate for ramping delays and other delays at other parts of the control system to improve stability of system operation.

The compensated pressure indication, Pc, is communicated to a step 134 at which the appropriate extraction or reinfusion flow rate limit curve from FIG. 2 is applied to system status parameters to generate a pressure error signal $P_E$. At step 134 a shifted or scaled flow rate count signal which represents actual velocity for blood pump 26 is mathematically applied to the equation representing the appropriate flow rate limit curve to generate the pressure at which the flow rate limit curve intersects the actual system flow rate to generate a limit pressure, $P_L$. A pressure error signal, $P_E$, is then generated as the difference between $P_C$ and $P_L$ with the sign of $P_E$ being positive if the actual pressure $P_C$ is within the limit point and negative if $P_C$ is beyond the limit point. In other words, for extraction $P_E = P_C - P_L$ and for reinfusion $P_E = P_L - P_C$ where $P_C$ and $P_L$ are signed real numbers. The net result, is a value for $P_E$ which increases negatively as flow rate increases beyond the point at which sensed pressure magnitude is outside the bounds of the flow rate limit curve during either extraction or reinfusion. It is noted that the motor M2 direction of rotation is independently controlled by processor 102 with only the speed of rotation being controlled by the adaptive flow rate control system 130.

At an integrator and limiter step 136 the pressure error value $P_E$ is integrated to help assure that any flow rate errors are corrected to zero. The integrated values are then limited to a selected maximum positive value corresponding to the current maximum flow rate value, which is determined and stored as previously described. Any negative value for the integrated pressure error signal (indicating that actual flow rate is beyond the acceptable limits) is limited to zero to avoid any improper response by the directionless speed magnitude control system. The integrated and limited pressure error signal is scaled by multiplication by ⅛ at a step 138 to assure scale compatibility with other system parameters.

The limited flow command, designated FL, is applied to an actual flow calibration step 144 during which the flow constant is utilized to calibrate the limited flow command, FL to produce a calibrated flow command signal FLC. As explained previously, a predetermined value is used for the first extraction-reinfusion cycle with value being determined from actual data during subsequent cycles. The noninvasive paristaltic pumps which are utilized to force fluid through the fluid flow path in plasmapheresis system 100 comprise four equally spaced rollers which squeeze flexible tubing defining the flow path between the rollers and a circular peripheral wall. The amount of fluid which is actually pumped during a quarter turn of the pump head depends on how much fluid is within the flow path between two adjacent rollers rotating against the peripheral wall. This quantity of fluid in turn depends upon the exact inside diameter of the flow path tubing and since the tubing must inherently be somewhat flexible and resilient, depends also upon the pressure of the fluid and the exact elasticity of the tubing. Since different sets of disposable tubing are utilized for each plasmapheresis operation and since system pressures are not always identical for different plasmapheresis operations, small but significant variations occur in the relationship between the velocity of blood pump 26 which is sensed by the adaptive flow rate control system 130 and the actual fluid flow rate.

By calibrating the limited flow command, FL, during extraction, the volume of plasma which is removed from the blood of the subject donor plasma separator 48 can be optimized.

The calibrated FL signal is applied to an acceleration limiting command table step 146. The acceleration limiting command table includes a 256 word by 8 bit lookup table and an indexing or counting register which stores an address for accessing the lookup table.

The counter register is controlled to be incremented or decremented one count at a time in response to the calibrated flow command signal FLC. If FLC is greater than the counter value, the counter is incremented by one. If FLC is less than the counter value, the counter is decremented by one. The counter value is then used to access the lookup table to produce a table value. Then an adjusted flow control signal, AFC, is updated using either the table value of signal FLC, or FLC itself, whichever results in the smallest change in magnitude of signal AFC from the current magnitude determined from the previous update cycle.

For larger flow values the table value can change by several units for each increment in the counter value. By using the smaller change produced by FLC or the table value, signal AFC can stabilize under steady state conditions at values intermediate the table values to provide more precise velocity control.

The table of values for acceleration limiting command table 146 is exponential in nature. The table produces values of 0, 9, 10, 11 for inputs of 0, 1, 2 and 3 respectively. The zero assures that zero input produces a zero output while the jump to 9 at the next step compensates for offsets in the particular D-A converter 106. Each step in the table increments by 1.03 over the previous step. For small input address values this step rounds to one. For larger values around 100 the step accordingly becomes 3.

The exponential relationship built into the table enables it to be used to control all three pumps 14, 26, 40 and hence reduce memory requirements. If the table were linear, AC pump 14 and cell pump 40 would accelerate proportionately more rapidly than blood pump 26. For example, full speed for blood pump 26 might correspond to FLC=90 and would require 90 update cycles for blood pump 26 to accelerate to full speed. The slower AC pump 14 and cell pump 40 might require FLC=30 or 40 and thus reach full speed in 30 or 40 update cycles. These pumps would then be running proportionately fast during the remaining 60 or 50 counts required for blood pump 26 to accelerate to full speed. The exponential table relationship enables speed changes in all three pumps 14, 26 and 40 to remain approximately in proportion while using a single lookup table for all of them.

At a subtraction step 148 the shifted flow rate count cycle for the latest 50 msec update interval is subtracted from the newly calculated adjusted flow rate command signal to generate a flow rate error signal, FRE, equal to the difference between the adjusted flow rate command signal and the actual flow rate. The flow rate error signal is integrated at an integrator step 150 and scaled by multiplication by ⅛ at a scaler step 152 prior to presentation to the digital-to-analog converter 106 (see FIG. 3). Digital-to-analog converter 106 converts the integrated and scaled flow rate error signal to an analog flow rate error signal which is applied to a PWM motor control circuit 160. PWM motor control circuit 160 includes a wide bandwidth PWM motor drive circuit of conventional nature and in effect represents a wide bandwidth servo loop within a narrower bandwidth digital servo loop.

Blood pump motor M2 has attached thereto a Hall effect sensor arrangement which produces 12 output pulses for each 360° of rotation of motor M2. These pulses are detected and counted at a pulse step 162. The pulse count outputs are applied to a subtractor step 164 and a multiply by 8 scaler step 166 to generate the shifted flow rate counts which are applied to the extraction and reinfusion curves 134 and the subtractor 148. Pulse counter 162 produces an output which represents motor rotational position. Subtractor 164 in effect operates as a differentiator to convert the position signal to a velocity signal by subtracting a previous count from a current count to produce a count difference corresponding to velocity. This difference is scaled by scaler 166 to generate the shifted flow rate counts signal.

The adaptive flow rate control system 130 thus operates on 50 msec repetitive update cycles during extraction or reinfusion to control the velocity of motor M2 which drives blood pump 26 to assure that bodily fluid flow either to or from the donor subject occurs at the maximum possible rate without exceeding the accommodation capability of the donor subject or the 100 ml per minute design limit of the system. This optimization of the bodily fluid flow rate assures optimum utilization of the equipment and minimum inconvenience and discomfort to the donor subject while precluding vein collapses which might occlude the needle during extraction or excessive pressure during reinfusion.

During normal stoppage of pumps 14, 26 and 40, the normal control algorithm shown in FIG. 7 is partially bypassed with the output of integrator and limiter 136, the output of integrator 150 and the index counter for acceleration limiting command table 146 all being set directly to zero in each of the control algorithms for the three pumps. If an emergency shutdown is executed, as when a negative value of 20 or more for the output of integrator and limiter 136 indicates that the actual operating point is far outside the appropriate flow rate limit curve, the blood pump motor is merely given a reverse direction command until an update cycle produces a shifted flow rate counts signal of zero. This suggests a very low or zero velocity. Then the normal stop procedure is executed as described above.

Whenever the integrator and limiter 136 outputs an error value of 20 or more during an extraction cycle the occurrence of an occlusion is suggested. In order to reduce the probability of additional occlusions occurring as soon as the system returns to full speed, the current maximum flow rate value is reduced by 10 ml per min, but not below some minimum threshold value such as 60 ml per min. If a donor cannot supply blood at the minimum threshold value it is presumed that either the needle 12 is not properly inserted or else that the donor is not a suitable donor.

As the current maximum flow rate value is adjusted downward an occlusion indicator flag is set. As shown in FIG. 5, each time the system begins an extraction cycle, the system examines the occlusion flag and performs an update. If the flag is set, indicating an occlusion during the preceding extraction cycle, the flag is reset. If the flag is not set, indicating that a complete extraction cycle has been executed without an occurrence of an occlusion, the current maximum flow rate value is increased by 5 ml per min, but not above the operator selected flow rate value and not above the inherent system maximum flow rate value of 100 ml per min.

The adaptive flow rate control system 130 thus operates to maintain bodily fluid flow rate as high as possible without exceeding the accommodation capability of the donor subject or the 100 ml per minute design flow rate of the plasmapheresis system 100. The control system 130 thus assures maximum utilization of the equipment and minimum inconvenience and discomfort to the donor subject while protecting against occlusion of the needle 12 because of vein collapse or tissue damage from excessive intravenous pressure.

While there has been shown and described above an adaptive flow rate control system which is particularly useful for controlling bodily fluid flow rates in a plasmapheresis system for the purpose of enabling a person of ordinary skill in the art to make and use the invention, it will be appreciated that the invention is not limited thereto. Accordingly, any modifications, variations or equivalent arrangements within the scope of the attached claims should be considered to be within the scope of the invention.

What is claimed is:

1. A system for controlling a flow of fluid in a given direction to or from a subject having a limited flow rate accommodation comprising:
   a fluid pump that is connectable in fluid pumping relationship along a fluid flow path between the subject and a fluid reservoir;
   a pressure sensor coupled to sense pressure in the fluid flow path between the fluid pump and the subject and generate an indication of the sensed pressure;
   a flow rate indicator coupled to provide an indication of fluid flow rate along the fluid flow path; and
   a fluid pump control system coupled to receive the sensed pressure and flow rate indications and provide to the fluid pump flow rate control signals in response thereto, the fluid pump control system including means for generating a flow rate limit curve by generating at least one test point flow rate command signal commanding respectively at least one test point flow rate that is anticipated to be within the flow rate accommodation of the subject, means for receiving from the pressure sensor an indication of the flow path pressure at each test point flow rate, means for generating a flow rate limit curve as an extrapolation of the received test point flow rate pressure indication received for each test point flow rate and a translation corresponding to an acceptable intravenous pressure change within the subject and means for generating during conditions of normal operation flow rate control signals limiting the actual flow rate to a magnitude within the flow rate limit curve.

2. The system for controlling according to claim 1 above, wherein the given direction is away from the subject and the translation pressure change is approximately a difference between a zero flow rate sensed pressure and a pressure of 6 mm Hg above atmospheric pressure.

3. The system for controlling according to claim 1 above, wherein the given direction is toward the subject and the translation pressure change is approximately a difference between a zero flow rate sensed pressure and a pressure of 56 mm Hg above atmospheric pressure.

4. The system for controlling according to claim 1 above, wherein the at least one test point flow rate includes at least the two different test point flow rates and the two different test point flow rates are zero and 50 ml per minute.

5. The system for controlling according to claim 1 above, wherein the extrapolation of the test point data is a linear extrapolation from at least two test point flow rates.

6. The system for controlling according to claim 1 above, wherein the fluid pump control system includes a digital processor coupled to receive the sensed pressure and flow rate indications and generate the fluid pump flow rate control signals and a flow rate control servo subsystem coupled to receive the flow rate control signals and energize the fluid pump for operation at the commanded rate.

7. The system for controlling according to claim 6 above wherein the digital processor is programmed to execute a repetitive flow rate update cycle in which the processor updates the sensed pressure indication from the pressure sensor, updates the flow rate indication from the flow rate indicator, calibrates the sensed pressure indication with respect to atmospheric pressure, generates an updated compensated pressure indication as a function of the calibrated pressure indication and a prior compensated pressure indication, calculates a pressure error value as a difference between the compensated pressure and the pressure value where the flow rate limit curve intersects the updated flow rate, integrates the pressure error value, additively combines the integral of the pressure error value with a nominal flow rate command to generate a flow rate command, imposes a lower flow rate of zero and a selected maximum upper flow rate upon the flow rate command to generate a limited flow rate command, adjusts the limited flow rate command by limiting a rate of change thereof and applies the adjusted flow rate command to the flow rate control servo subsystem as a flow rate control signal.

8. The system for controlling according to claim 7 above, wherein the flow rate indicator provides an indication of rotation of the fluid pump and the digital processor is further programmed to use a flow rate constant to relate fluid flow to indicated fluid pump rotation, and to update the flow rate constant by pumping a predetermined quantity of fluid while determining the number of fluid pump rotations required to pump the known quantity with the updated flow rate constant being determined in response to the ratio of the predetermined fluid quantity to the determined number of fluid pump rotations.

9. The system for controlling according to claim 7 above, wherein the fluid pump is a paristaltic pump which does not contaminate a sterile fluid flow path environment.

10. The system for controlling according to claim 7 above, wherein the digital processor limits the rate of change of the limited flow rate command to 0.03 per update cycle.

11. The system for controlling according to claim 1 above, wherein the fluid pump control system generates the fluid pump flow rate control signals in response to a difference between actual sensed fluid pressure at a point along the fluid flow path between the fluid pump and the subject and the pressure value on the flow rate limit curve for the current actual fluid flow rate.

12. An adaptive blood flow control system for extracting blood from a subject donor at an optimum rate during a plasmapheresis operation comprising:
 tubing defining a blood flow path between a donor attachment and a reservoir for receiving blood, the tubing being suitable for replacement after each plasmapheresis operation;
 a blood pump disposed to pump blood along the blood flow path at a commanded rate and provide a signal that is indicative of the instantaneous actual flow rate;
 a pressure sensor disposed to detect and indicate blood pressure in the blood flow path at a point upstream from the blood pump; and
 a control system including a data processor coupled to receive the indications of pressure and actual flow rate and in response thereto provide flow rate commands to the blood pump, the control system data processor receiving sensed pressure data at a first flow rate test point, receiving sensed pressure data at a second flow rate test point different from the first test point, generating a flow rate limit curve in response to the received sensed pressure data at the first and second flow rate test points and commanding a maximum pumping rate limited by a nominal maximum rate or a dropping of sensed pressure below the flow rate limit curve, whichever occurs at a lower pumping rate.

13. The adaptive blood flow control system according to claim 12 above, wherein the control system data processor extrapolates the test point data to generate a first curve, generates a second curve translated relative to the first curve by a selected amount corresponding to an intravenous pressure change that is deemed to be acceptable, and derives the flow rate limit curve from the second curve.

14. The adaptive blood flow control system according to claim 13 above, wherein the data processor derives the flow rate limit curve from the second curve by rotating the second curve about the nominal maximum rate intercept point in a direction decreasing the allowable pressure drop at low flow rates.

15. The adaptive blood flow control system according to claim 14 above, wherein the flow rate limit curve intercepts the zero flow rate point at a pressure that is approximately 16 mm Hg below the zero flow rate intravenous pressure of the subject donor.

16. An adaptive bodily fluid flow rate control system for extracting bodily fluid from a living subject at an optimum rate comprising:
 a fluid pump disposed along a fluid flow path to pump intravenous bodily fluids along the flow path between a living subject and a reservoir at a commanded rate and generate an actual flow rate signal that is indicative of the instantaneous actual flow rate;
 a pressure sensor disposed to detect actual fluid pressure in the fluid flow path on a side of the fluid pump adjacent the living subject and generate an actual pressure signal indicative of the sensed pressure; and
 a control system coupled to receive the actual flow rate signal and actual pressure signal and provide flow rate commands to the fluid pump in response thereto, the control system including means for deriving first test point pressure data from the actual pressure signal at a first test point flow rate, deriving second test point pressure data from the actual pressure signal at a second test point flow rate different from the first test point flow rate, extrapolating and translating the first and second test point data to generate a flow rate limit curve defining pressure limits for optimizing the flow rate for the living subject, and commanding a maximum pumping rate for an optimum bodily fluid flow rate, the pumping rate being limited to prevent actual sensed pressure from exceeding the flow rate limit curve.

17. The adaptive bodily fluid flow rate control system according to claim 16 above, wherein the reservoir is a plasmapheresis system.

18. An adaptive fluid flow control system optimizing a reinfusion fluid flow rate in a plasmapheresis system, the fluid flow control system comprising:
 apparatus defining a sterile, noninvasive fluid flow path between an intravenous coupling to a living subject and a reservoir of a plasmapheresis system;
 a noninvasive fluid pump disposed along the fluid flow path to pump fluid therethrough at a rate responsive to a pump flow rate command;
 a pressure sensor coupled to sense pressure in the fluid flow path between the fluid pump and the intravenous coupling and generate a pressure indication signal representative of the sensed pressure; and a flow rate controller coupled to receive the pressure indication signal and generate the pump flow rate command in response thereto, the flow rate controller including means for generating two different test point flow rate command signals to cause two different fluid flow rates through the fluid flow path, means for determining sensed pressure from the pressure indication signal at the resulting two different test point flow rates, and means for extrapolating the sensed pressure into a flow rate curve, translating the flow rate curve by an amount equal to an acceptable change in intravenous pressure to generate a second curve, deriving a flow rate limit curve from the second curve, and generating the flow rate command to produce a maximum fluid flow rate limited to a flow rate at which the sensed fluid pressure is not outside the flow rate limit curve.

19. The adaptive fluid flow control system according to claim 18 wherein the means for extrapolating, translating, deriving and generating further includes means for limiting the commanded flow rate to a predetermined nominal maximum flow rate.

20. The adaptive fluid flow control system according to claim 18 above, wherein the flow rate controller is a programmed digital processor.

21. A method of controlling a flow rate of bodily fluids along a flow path between a subject and a reservoir comprising the steps of:
sensing pressure data along the flow path at two different test point flow rates known to produce minimal change in intravenous pressure in the subject;
generating a flow rate limit curve in response to an extrapolation of the sensed pressure data, the flow rate limit curve representing sensed extravenous pressures corresponding to acceptable intravenous pressure limits within the subject as a function of fluid flow rate; and
pumping bodily fluid along the flow path while sensing the fluid pressure, the pumping being controlled to limit the bodily fluid flow rate to a rate at which the magnitude of the sensed fluid pressure is less than the magnitude of the pressure intercepted by the flow rate limit curve at any given flow rate.

22. The method of controlling a flow rate according to claim 21 above, wherein the acceptable intravenous pressure limit is approximately 50 mm Hg for a flow direction toward the subject.

23. The method of controlling a flow rate according to claim 21 above, wherein the acceptable intravenous pressure limit is approximately 6 mm Hg for a flow direction away from the subject.

24. A method of controlling a flow rate of bodily fluids along a flow path between a subject and a reservoir comprising the steps of:
sensing pressure data along the flow path at two different test point flow rates known to produce minimal change in intravenous pressure in the subject;
generating a flow rate limit curve in response to an extrapolation of the senses pressure date, the flow rate limit curve representing sensed extravenous pressures corresponding to acceptable intravenous pressure limits within the subject as a function of fluid flow rate, the generating step including the steps of linearly extrapolating the sensed pressure data to generate a flow rate curve representing sensed flow path pressure as a function of fluid flow rate at a constant intravenous pressure and translating the flow rate curve by a magnitude equal to a maximum acceptable change in intravenous pressure to generate the flow rate limit curve; and
pumping bodily fluid along the flow path while sensing the fluid pressure, the pumping being controlled to limit the bodily fluid flow rate to a rate at which the magnitude of the sensed fluid pressure is less than the magnitude of the pressure intercepted by the flow rate limit curve at any given flow rate.

25. The method of controlling a flow rate according to claim 24 above, wherein the flow rate limit curve has the form $$P = M(FR) + PG + PZ$$

where P is the fluid flow path pressure, M is a rate of change of flow path pressure with respect to flow rate determined from the test point data, PC is the maximum acceptable intravenous pressure change, and PZ is a zero flow rate flow path pressure determined from the test point data.

26. A method of controlling a flow rate of bodily fluids along a flow path between a subject and a reservoir comprising the steps of:
sensing pressure data along the flow path at at least two different test points having different flow rates that are known to produce minimal change in internal pressure in the subject;
generating a flow rate limit curve in a coordinate representation having a pressure axis and a flow rate axis in response to the sensed data by generating the flow rate limit curve as a curve that has a selected relationship to and is different from a full pressure-flow rate curve passing through the test points; and
pumping bodily fluid along the flow path while sensing the fluid pressure, the pumping being controlled to produce a bodily fluid flow rate tending to minimize any difference between a sensed fluid pressure at a current flow rate and a pressure intercept of the flow rate limit curve at the current flow rate.

27. The method of controlling according to claim 26 wherein the step of generating a flow rate limit curve includes the steps of translating the flow rate limit curve relative to the full pressure flow rate curve and rotating the flow rate limit curve relative to the test curve.

28. The method of controlling according to claim 26 wherein the steps of generating includes selecting at least two points on the full pressure flow rate curve, translating the selected points to produce translated points and generating the flow rate limit curve as a curve passing through the translated points.

29. The method of controlling according to claim 28 wherein the selected points are translated toward a lesser pressure value and a first selected point at a first flow rate is translated by a greater amount than a second selected point at a second flow rate greater than the first flow rate.

30. The method of controlling according to claim 26 wherein the flow rate limit curve is effectively rotated clockwise relative to the full pressure flow rate curve.

31. The method of controlling according to claim 26 wherein the flow rate limit curve is effectively rotated counterclockwise relative to the full pressure flow rate curve.

32. The method of controlling according to claim 26 further comprising the step of limiting the rate at which bodily fluid is pumped in accordance with a current flow rate limit value.

33. The method of controlling according to claim 26 further comprising the steps of:
limiting the rate at which bodily fluid is pumped in accordance with a current flow rate limit value;
receiving an operator selected flow rate limit value; and
limiting the current flow rate limit value to the received operator selected flow rate limit value.

34. The method of controlling according to claim 33 further comprising the step of constraining the operator selected flow rate limit value to be within a selected range.

35. The method of controlling according to claim 32 further comprising the execution during an extraction cycle of the steps of:
increasing the current flow rate limit value, subject to any upper limit therefor, when no occlusion of bodily fluid flow has occurred during an immediately preceding extraction cycle;
setting an occlusion indicator flag upon the occurrence of an occlusion of bodily fluid flow; and
decreasing the current flow rate limit value, subject to any lower limit thereon, upon an occurrence of an occlusion of bodily fluid flow.

36. The method of controlling according to claim 35 wherein an amount by which the flow rate limit value is increased when there is no occlusion is less than an amount by which the flow rate limit value is decreased upon an occurrence of an occlusion.

37. The method of controlling according to claim 26 wherein the generated flow rate limit curve is for a first flow direction relative to the subject and further comprising the step of generating a second flow rate limit curve for a second fluid flow direction opposite the first direction, the slopes of the first and second fluid fluid flow direction flow rate limit curves differing by a multiplying factor in the range of −1 to −3.

38. The method of controlling according to claim 37 wherein the multiplying factor is −1.5.

39. The method of controlling according to claim 37 wherein the multiplying factor is −2.

40. The method of controlling according to claim 37 wherein the slope of the flow rate limit curve is negative for an extraction flow direction and positive for a reinfusion flow direction.

41. The method of controlling according to claim 37 wherein the flow rate limit curve for a flow direction toward the subject has a positive slope and a positive offset at a zero flow rate point relative to a zero flow rate fluid pressure.

42. The method of controlling according to claim 41 wherein the positive offset is substantially 48.

43. An adaptive bodily fluid flow control system comprising:
a bodily fluid flow path defined between a subject and a reservoir;
a pump disposed to pump bodily fluid along the bodily fluid flow path at a rate commanded by a flow rate command signal;
a pressure sensor disposed to detect and indicate fluid pressure in the fluid flow path at a location between the pump and the subject;
a control system including a data processor that is coupled to receive current indications of current pressure from the pressure sensor and to control the pump in response thereto, the data processor commanding at least two different test point flow rates which are known to produce little fluid pressure drop internally of the subject and receiving from the pressure sensor and storing test point pressure indications at each of the test point flow rates to establish at least two test points in a coordinate system having a pressure axis and a flow rate axis, the data processor further establishing a full pressure flow rate curve passing through the test points, a flow rate limit curve that is selectively translated and selectively rotated relative to the full pressure flow rate curve, and generating a flow rate command signal tending to reduce any difference between a currently sensed pressure and a pressure intercept of the flow rate limit curve at a current fluid flow rate.

44. The adaptive bodily fluid flow control system according to claim 43 wherein the flow rate limit curve is rotated counterclockwise through an acute angle relative to the full pressure flow rate curve.

45. The adaptive bodily fluid flow control system according to claim 43 wherein the flow rate limit curve is rotated clockwise through an acute angle relative to the full pressure flow rate curve.

46. The adaptive bodily fluid flow control system according to claim 43 wherein the data processor stores a current maximum flow rate value and limits the flow rate commanded by the flow rate command signal to the current maximum flow rate value.

47. The adaptive bodily fluid flow control system according to claim 46 wherein the data processor receives and stores an operator selected maximum flow rate value and limits the current flow rate value to the operator selected flow rate value.

48. The adaptive bodily fluid flow control system according to claim 46 wherein the system operates during a plurality of sequential extraction cycles and wherein the data processor stores an occlusion flag, performs an update sequence at the beginning of each extraction cycle by increasing the stored current maximum flow rate value, subject to any upper limits, when the occlusion flag indicates no flow occlusion occurred during an immediately preceding extraction cycle, decreasing the current flow rate value whenever an occlusion occurs during an extraction cycle and setting the occlusion flag whenever an occlusion occurs during an extraction cycle.

* * * * *